(12) United States Patent
Antonino (10) Patent No.: US 10,201,630 B2
(45) Date of Patent: *Feb. 12, 2019

(54) AROMATHERAPY APPARATUS AND HOUSING

(71) Applicant: Jason Carl Antonino, Phoenix, AZ (US)

(72) Inventor: Jason Carl Antonino, Phoenix, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/902,958

(22) Filed: Feb. 22, 2018

(65) Prior Publication Data

US 2018/0193512 A1 Jul. 12, 2018

Related U.S. Application Data

(63) Continuation-in-part of application No. 15/059,294, filed on Mar. 2, 2016, now Pat. No. 9,950,089.

(51) Int. Cl.
*A61L 9/12* (2006.01)
*A47G 9/00* (2006.01)
(Continued)

(52) U.S. Cl.
CPC .............. *A61L 9/12* (2013.01); *A47G 9/007* (2013.01); *A47G 9/0253* (2013.01);
(Continued)

(58) Field of Classification Search
CPC ........... A61L 9/12; A47G 9/10; A47G 9/1009; A47G 9/1045
See application file for complete search history.

(56) References Cited

U.S. PATENT DOCUMENTS 5,266,070 A 11/1993 Hagiwara et al.
5,353,211 A 10/1994 Merko
(Continued)

FOREIGN PATENT DOCUMENTS

CN 201438997 U 4/2010
KR 101215009 B1 12/2012
(Continued)

*Primary Examiner* — Kristen Matter (57) ABSTRACT

The present invention is an apparatus for employing aromatherapy, binaural sounds, music, vibration, and visual effects for altering a user's emotional state. The apparatus comprises: a shape memory foam pillow, a pair of stereo speakers, an aromatherapy diffuser, a pillowcase comprised of a temperature-regulating fabric, a vibrating device, a strobe light, a canopy, and a housing to integrate and support these components. The user connects a smartphone or other portable digital audio device to the speakers, activates the aromatherapy diffuser, strobe light, and vibrating device, independently or in combination, and then lays his head down on the pillow beneath the open canopy. Ideally, the smartphone or audio device should have a meditation, music, or binaural sound application, which would be tuned to a specific beat frequency, e.g. 10 Hertz. The combined action of essential oil vapors, binaural sounds or music, vibration, and strobe light should alter the user's emotional state towards relaxation, sleepiness, or increased alertness, depending on the essential oils, sounds, vibration, and light patterns employed.

15 Claims, 6 Drawing Sheets

(51) Int. Cl.
*A47G 9/02* (2006.01)
*A47G 9/10* (2006.01)
*A61M 21/00* (2006.01)
*A61M 21/02* (2006.01)
*A61M 23/00* (2006.01)
*A61H 23/00* (2006.01)

(52) U.S. Cl.
CPC ........... *A47G 9/1045* (2013.01); *A61H 23/00* (2013.01); *A61M 21/02* (2013.01); *A47G 2009/005* (2013.01); *A47G 2009/006* (2013.01); *A47G 2009/1018* (2013.01); *A61H 2201/50* (2013.01); *A61M 2021/0022* (2013.01); *A61M 2021/0027* (2013.01); *A61M 2021/0066* (2013.01)

(56) References Cited

U.S. PATENT DOCUMENTS

| | | | |
|---|---|---|---|
| 5,622,427 A | 4/1997 | Lemons et al. | |
| 6,023,801 A | 2/2000 | Lamm | |
| 6,702,767 B1 | 3/2004 | Douglas et al. | |
| 7,095,187 B2 | 8/2006 | Young | |
| 7,578,783 B2 | 8/2009 | Klein | |
| 8,070,669 B2 | 12/2011 | Brunelle et al. | |
| 8,566,986 B1 | 10/2013 | Chu | |
| 9,950,089 B2 * | 4/2018 | Antonino | A61L 9/12 |
| 2005/0288749 A1 | 12/2005 | Lachenbruch | |
| 2007/0011813 A1 | 1/2007 | Rathle | |
| 2007/0068515 A1 | 3/2007 | Churchill | |
| 2011/0061166 A1 | 3/2011 | Liu | |
| 2013/0254999 A1 | 10/2013 | Foch | |
| 2013/0270880 A1 | 10/2013 | Lee | |
| 2014/0008036 A1 | 1/2014 | Segal | |
| 2014/0053338 A1 | 2/2014 | White | |
| 2015/0016613 A1 | 1/2015 | Atwater et al. | |
| 2015/0025606 A1 | 1/2015 | Davis | |
| 2015/0047646 A1 | 2/2015 | Marinkovic | |
| 2015/0334482 A1 | 11/2015 | Rawls-Meehan et al. | |
| 2016/0055842 A1 | 2/2016 | DeFranks et al. | |

FOREIGN PATENT DOCUMENTS

| | | |
|---|---|---|
| WO | WO2009079694 A1 | 1/2009 |
| WO | WO2013020263 A2 | 2/2013 |

* cited by examiner

AROMATHERAPY APPARATUS AND HOUSING

CROSS-REFERENCE TO RELATED APPLICATIONS

This non-provisional application for patent is a Continuation-in-Part of U.S. Non-Provisional application Ser. No. 15/059,294, filed on Mar. 2, 2016, which claims priority under 35 U.S.C. 119 § (e) to U.S. Provisional Application No. 62/140,404, filed on Mar. 30, 2015, the contents of which are incorporated herein by reference in their entirety.

BACKGROUND OF THE INVENTION

The present invention relates to aromatherapy, particularly, the diffusion of essential oils in living quarters. Essential oils have been used in aromatherapy applications at various times throughout history. Essential oils of lavender, bergamot, clary sage, orange, and ylang-ylang, to name a few, have been used for treatment of nervous tension and inducing relaxation.

The present invention also relates to the use of binaural sounds for the purpose of altering emotional states. Binaural sounds are comprised of two separate sound channels vibrating at different frequencies, presented to a user simultaneously through headphones or speakers. The frequency difference between the two sounds is termed the binaural beat frequency, which is what the user experiences, and causes a corresponding shift in his brainwave frequency.

The present invention further relates to specially-shaped memory foam pillows for optimal support of a person's head, so as to ease muscle strain, thereby minimizing muscle tension.

The invention still further relates to a temperature-regulating fabric so as to keep a user's skin temperature constant, thereby making the user more comfortable.

The invention further relates to a vibrating element for providing a gentle massaging action to the user's head.

The invention further relates to a strobe light for providing visual effects in a pattern for the purpose of altering or influencing the emotional state of a user.

The invention relates to an overhead canopy for providing protection from sunlight and a degree of privacy.

Finally, the invention relates to a housing in the form of an open container for integrating and supporting the above elements.

Many types of aromatherapy diffusers are known in the art. They are typically comprised of a plastic reservoir to hold a mixture of water and one or more essential oils, an ultrasonic vibrating component, and a cover with an orifice through which essential oil vapors are directed. Some diffusers also display changing colors for ambience. The "Now® Ultrasonic Oil Diffuser" is such an example.

Binaural sound devices and applications are known in the art. They are typically marketed as software installed on desktop and portable computers for playing binaural soundtracks through stereo headphones or speakers. A state of relaxation or sleepiness can be induced by entraining a user's brainwaves from the wide-awake beta range downward into alpha, and then into theta. US 2015/0016613 A1 "Spatial angle modulation binaural sound system," to Fredrick Atwater, et al., discloses a method of inducing a state of consciousness in a listener by providing first and second sound signals to a user's left and right ear, respectively.

Contoured shape memory foam pillows are also well known in the art. US 2015/0047646 A1 "Therapeutic pillow," to John Marinkovic, discloses a contoured pillow for neck support and correction. The "Sleep Innovations Contour Memory Foam Pillow," sold through Amazon.com, relieves neck, shoulder and back pain by allowing neck and shoulder muscles to fully relax, and the pillow promotes proper spinal alignment. Many other entities market and sell similar pillows.

Systems and methods for cooling a pillow exist in the art. For example, US 2015/0025606 A1 "Pillow integrated cooling system," to James Elliott Davis, discloses a system that can constantly transport a fluid throughout a pillow in order to keep the fluid at a desired temperature. The system uses fluid from a tank or reservoir that can be heated or cooled by a radiator prior to being filtered and distributed through tubes placed in the interior of the pillow.

US 2014/0053338 A1 "Aromatic air effusion apparatus for a pillow," to Chester Lewis White, discloses an aromatic air effusion apparatus for a pillow for both leisure relaxation and sleep retirement at night. The apparatus provides a user with a variety of aromatic scents that can be mechanically diffused throughout the interior of the pillow.

U.S. Pat. No. 5,353,211 A "Light modifier," to Andrew Merko, discloses a combined modeling/strobe light source for illuminating a subject.

U.S. Pat. No. 6,702,767 B1 "Multisensory stimulation system and method," to Douglas Nelson, et al. discloses a housing with a support for a user, and a viewing chamber through which the user can view light and images projected from monitors, projectors, or strobe lights. The invention also includes an aromatic sensory component, tactile sensation devices, and audio input and delivery devices.

U.S. Pat. No. 7,095,187 B2 "LED strobe light," to Garrett Young, discloses an LED strobe light with novel driving circuitry.

U.S. Pat. No. 7,578,783 B2 "Sensory experience method and apparatus," to Jurgen Klein, discloses an apparatus and method for providing sensory stimulation to a user floating in a pool of liquid. A sequence of fine water droplets with essential oil is directed into the atmosphere above the user with matching color of light and sound.

At this time, there are no known aromatherapy devices that combine the benefits of essential oil diffusion with binaural sounds, music, vibration, visual effects, temperature-regulating fabric, a canopy, and a portable housing. This invention provides all of these desirable features in a sturdy housing with a reduced footprint that can be used by an individual user without requiring the assistance of another person to set up and configure the device. Because users supply their own smartphones or digital audio devices, they can provide music or sounds of their own liking.

SUMMARY OF THE INVENTION

This is an aromatherapy apparatus that combines the features of essential oils diffused into the air, binaural sounds or music provided by a pair of stereo speakers, a contour shape memory foam pillow with a temperature-regulating fabric pillowcase, a vibrating element disposed inside or outside the pillowcase, a strobe light, a housing to support these features, and a canopy disposed over the apparatus to provide privacy and a projection surface for the strobe light.

These and other aspects and advantages of the invention will become apparent to those with ordinary skill in the art through the following description and drawings, which illustrate the features of the present invention.

DETAILED DESCRIPTION OF THE INVENTION

This is an aromatherapy apparatus that combines the features of essential oils diffused into the air, binaural sounds and/or music provided by a pair of stereo speakers, a contour shape memory foam pillow with a temperature-regulating fabric pillowcase to keep the user cool, a vibrating element disposed inside or outside the pillowcase, a visual strobe light, and a housing to support said features, and a canopy disposed over the apparatus to provide privacy and a projection surface for the strobe light.

Figure 1:
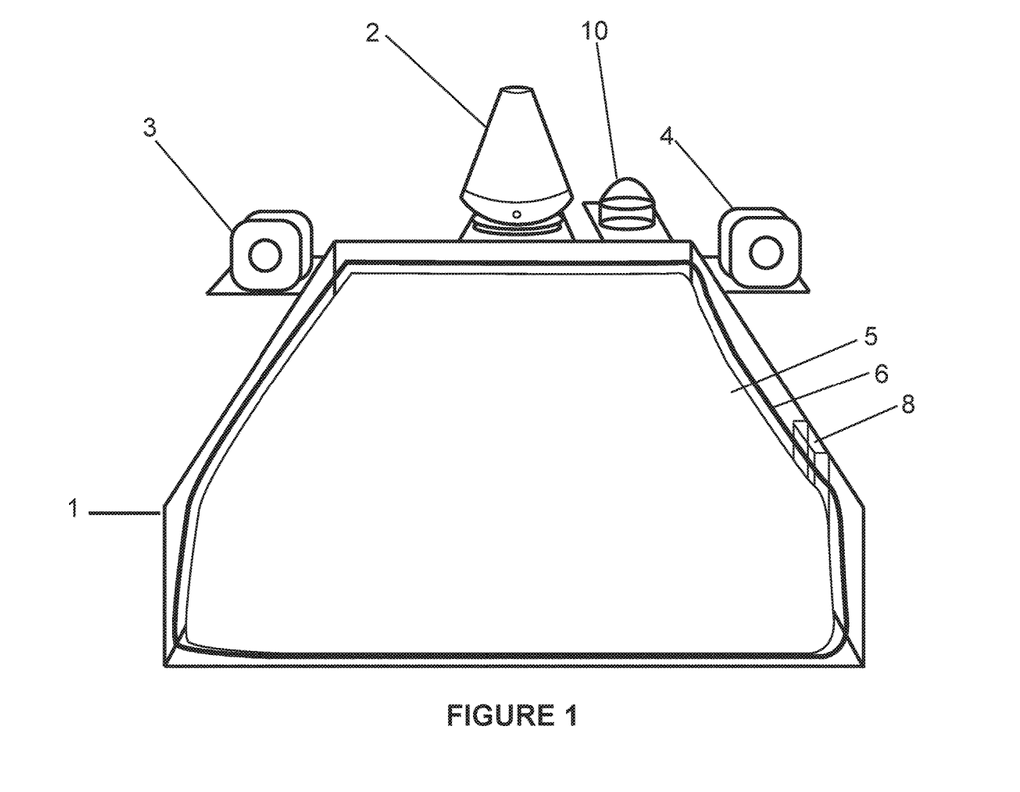
FIG. 1 is a perspective view of the fully assembled apparatus without the canopy.

FIG. 1 shows a perspective view of the preferred embodiment of the invention. The apparatus includes a housing 1, aromatherapy diffuser 2, left speaker 3, right speaker 4, contour shape memory foam pillow 5 disposed inside pillowcase 6, input cable 7 (not shown) for insertion into a smartphone or other digital device (not shown), vibrating element 8, canopy 9 (not shown), and visual strobe light 10 with handheld remote 11 (not shown). The elements not shown in FIG. 1 appear in subsequent drawings.

The housing 1, in this embodiment, was fabricated from oriented strand board (OSB), which is an engineered wood particle board formed by adding adhesives and then compressing layers of wood strands (flakes) in specific orientations. The OSB in this invention was purchased from The Home Depot, although one of ordinary skill in the art would understand that this material can be obtained from a plurality of sources. Further, one of ordinary skill would also appreciate that other materials can be used to fabricate the housing, such as high-density polyethylene or other plastics.

Figure 2:
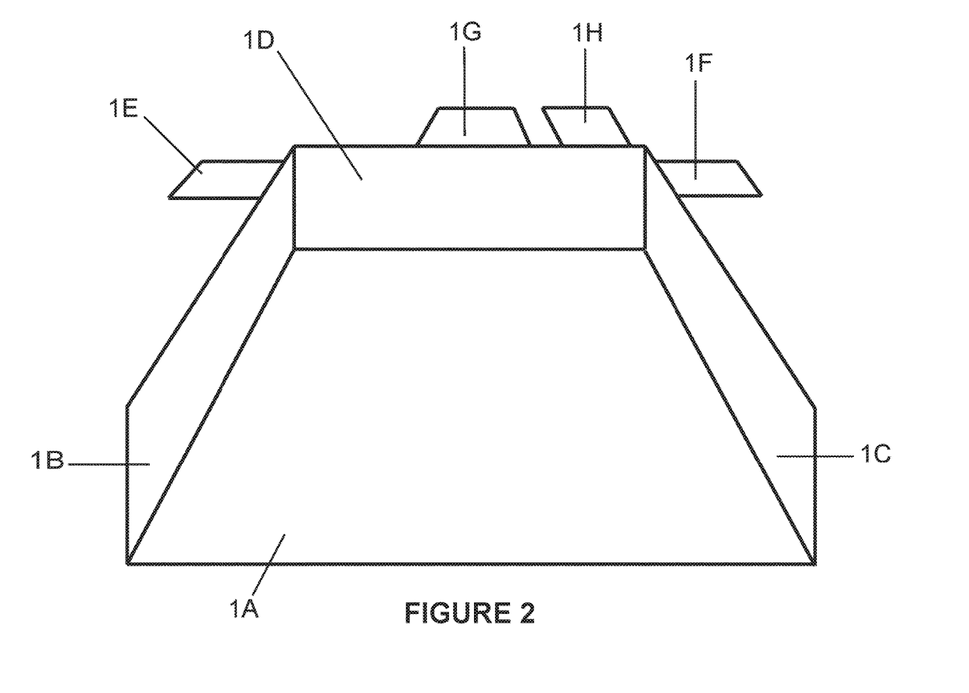
FIG. 2 is a view of the empty housing.

The housing 1 consists of eight pieces: a bottom wall, a left wall, a right wall, a rear wall, a left speaker support, a right speaker support, a diffuser support, and a strobe light support. These elements were joined together using Gorilla Glue, although one of ordinary skill would understand that mechanical fasteners could also be used. The joints were reinforced with Gorilla Glue Tape. The left speaker support was joined to the left wall, the right speaker support to the right wall, and both the diffuser support and strobe light support to the rear wall. The vibrating element 8 is secured to the left or right wall with the clip on the rear of the vibrating element control housing. In the alternative, a user can simply hold the vibrating element 8 while in use.

One of ordinary skill would understand that the housing could be fabricated from a single injection-molded piece of plastic. This description is not intended to limit the types of materials that could be used to form the housing, and any number of pieces may be used to construct the housing, as long as proper support is provided to the speakers, diffuser, pillow, vibrating element, strobe light, and canopy.

FIG. 2 is a view of the housing 1. The bottom is represented by 1A, the left wall 1B, right wall 1C, rear wall 1D, left speaker support 1E, right speaker support 1F, diffuser support 1G, and strobe light support 1H.

Figure 3:
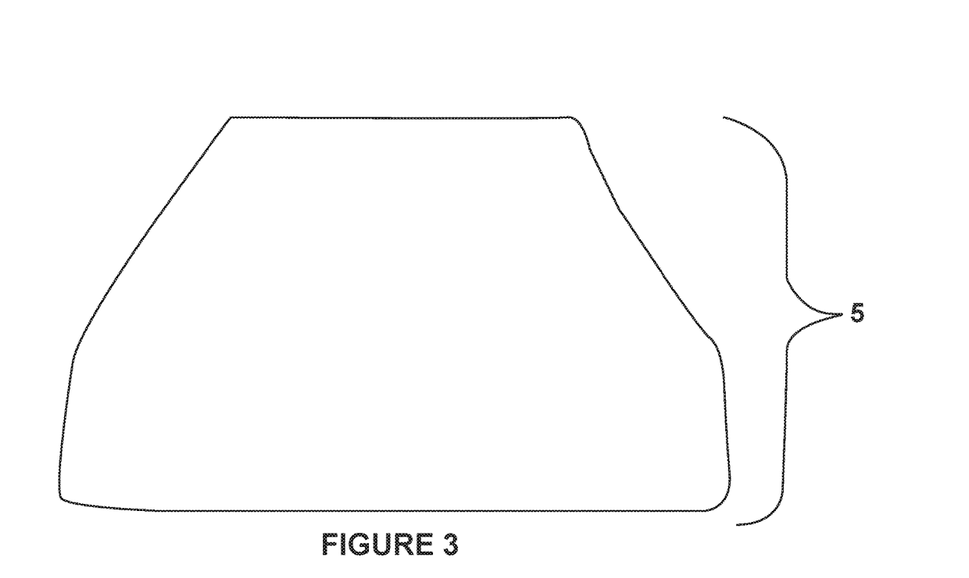
FIG. 3 is a view of the contour shape memory foam pillow.

FIG. 3 is a view of the contour shape memory foam pillow 5, in this example, the "Sleep Innovations Contour Memory Foam Pillow," purchased from Amazon.com.

Figure 4:
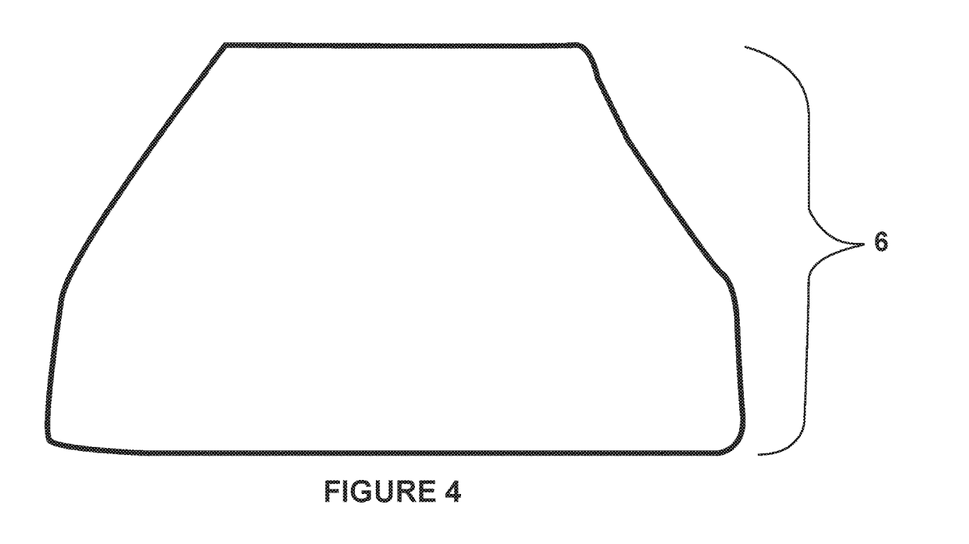
FIG. 4 is a view of the temperature-regulating fabric pillowcase.

FIG. 4 is a view of the temperature-regulating fabric pillowcase 6, in this example, the "Outlast White Standard Pillow Cover" manufactured by Outlast and purchased from Slumbercloud.com.

Figure 5:
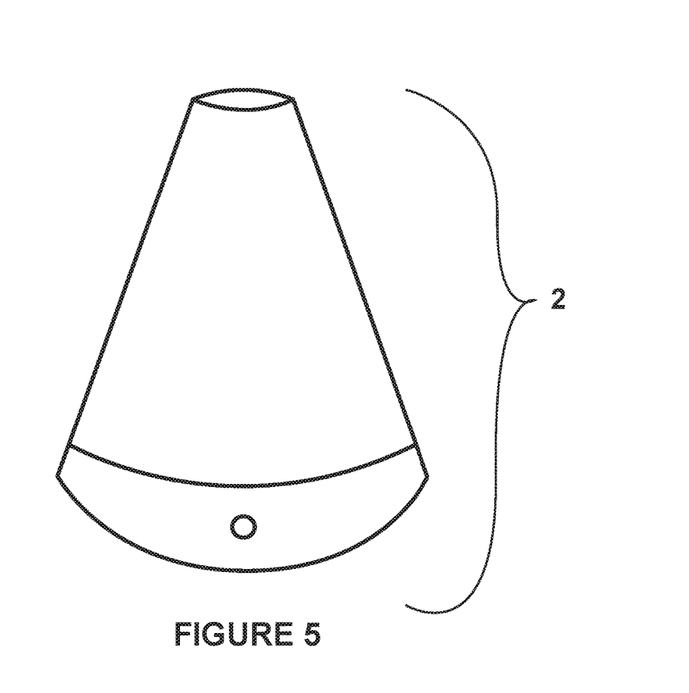
FIG. 5 is a view of the aromatherapy diffuser.

FIG. 5 is a view of the aromatherapy diffuser 2, in this example, "Now® Ultrasonic Oil Diffuser" purchased from Hi-Health.

Figure 6:
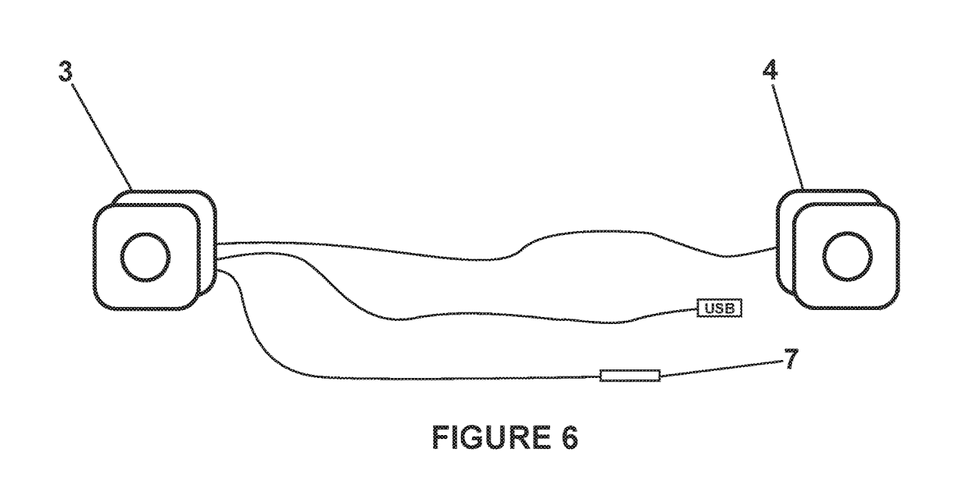
FIG. 6 is a view of the pair of stereo speakers and input jack.

FIG. 6 is a view of the set of stereo speakers 3 and 4, USB (Universal Serial Bus) power cable, and input cable 7 for insertion into a smartphone or portable digital music player (not shown). In this example, the "ARCTIC 5111 USB-Powered Portable Stereo Speakers" were purchased from Amazon.com.

Figure 7:
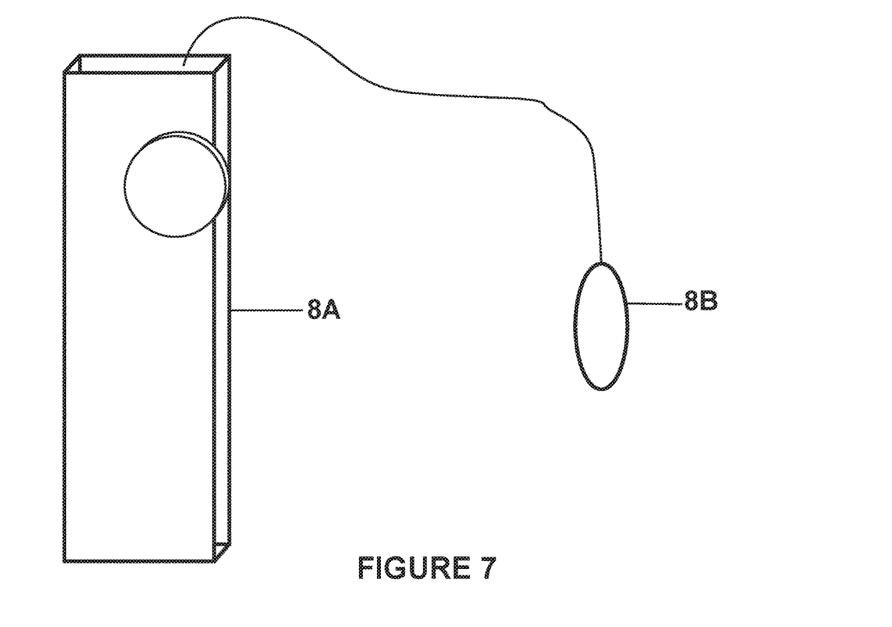
FIG. 7 is a view of the vibrating element.

FIG. 7 is a view of the vibrating element 8, in this example, manufactured and sold by Swedish Erotica. The vibrating element 8 consists of control 8A and vibrating egg 8B.

Figure 8:
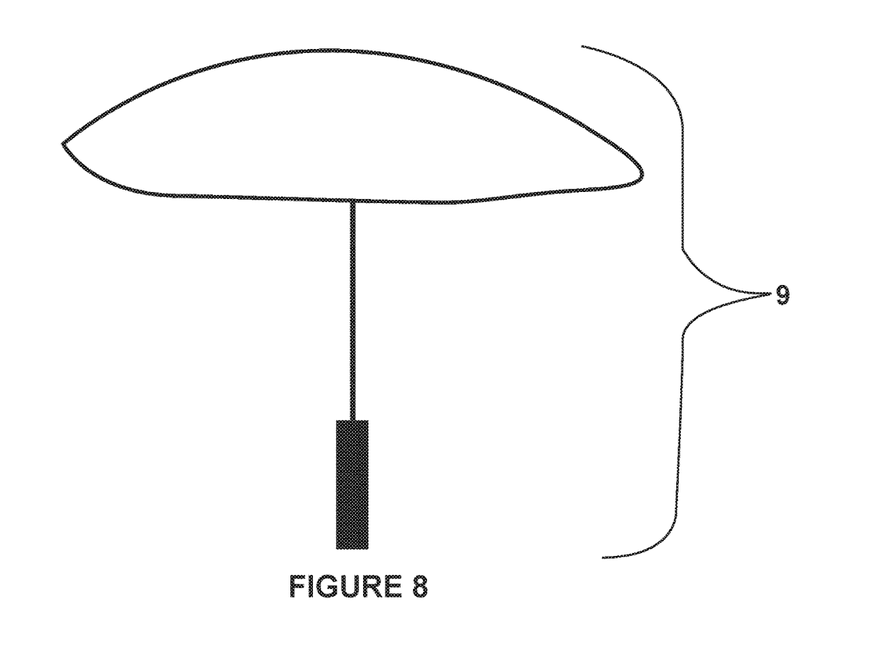
FIG. 8 is a view of the canopy.

FIG. 8 is a view of the canopy 9, in this example, a small umbrella, which can be obtained from most department stores.

Figure 9:
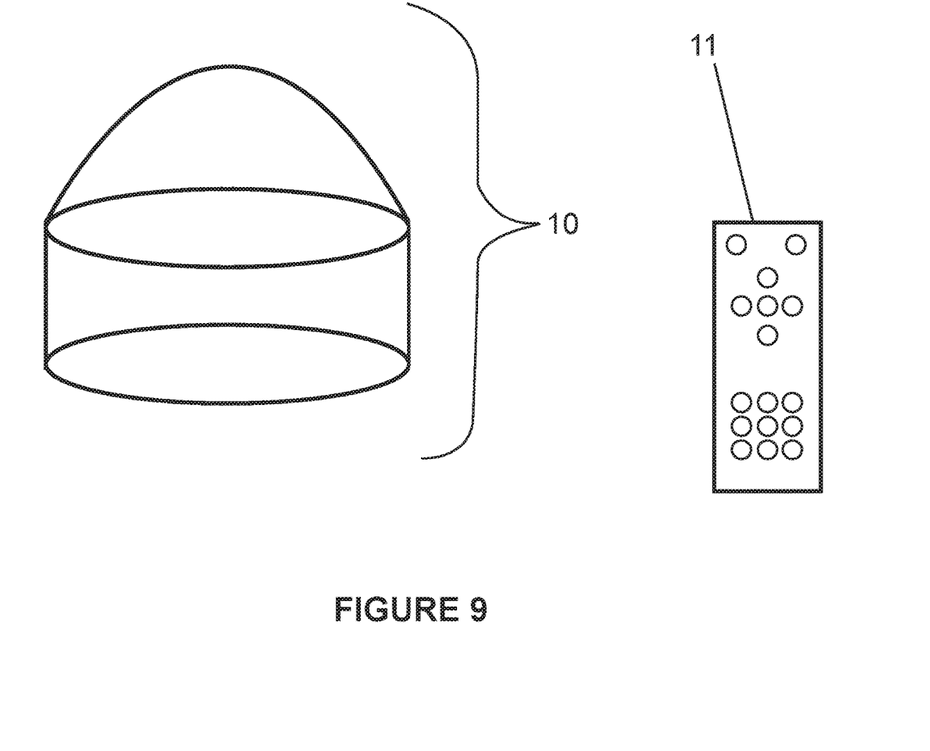
FIG. 9 is a view of the strobe light and remote.

FIG. 9 is a view of the strobe light 10 and remote 11, in this example, "Aolun Disco Lights Sound Activated with Remote," purchased from Amazon.com.

The aromatherapy diffuser 2, speakers 3 and 4, and strobe light 10 must first be plugged into a 120-volt AC electrical outlet, prior to using the apparatus. The aromatherapy diffuser 2 is placed on top of diffuser support 1G. The speakers 3 and 4 are placed on top of speaker supports 1E and 1F, respectively. The strobe light 10 is placed on top of strobe light support 1H. In the preferred embodiment, a power strip is utilized to make the process easier, however, this is not required. A power strip is not a part of the invention.

In normal operation, a user would add a small quantity of water and one or more essential oils to the reservoir in the diffuser 2. Essential oils used for relaxation include lavender, cedarwood, orange, bergamot, frankincense, ylang-ylang, etc., independently or in combination. After the water and essential oil(s) have been added, the user presses the button to turn on the diffuser. While several types of aromatherapy diffusers exist in the marketplace, for example, ultrasonic, nebulizing, plug-in, etc., a preferred embodiment of this invention utilizes ultrasonic diffusers due to their lower cost and that they are quieter than the nebulizing type of diffusers. Mechanical noise would interfere with the music or binaural beats output from the speakers 3 and 4.

The user then plugs the speaker input jack 7 into a user-provided smartphone, such as an iPhone, iPod, or other digital audio device, equipped with binaural sound software, a music player, or a meditation application. The invention does not include a smartphone or digital audio device. The user then accesses the desired software or app, and selects an appropriate meditation soundtrack or binaural beat frequency, ideally in the alpha range of 7 to 10 Hertz for relaxation, or within the theta range of 4 to 7 Hertz for sleep induction. Alternatively, a user could select a higher frequency (over 15 Hertz) for mental stimulation.

The canopy 9, if used, is secured to the rear wall 1D of the housing 1 so as to provide shade and a degree of privacy to the user.

The strobe light 10 is disposed on top of the strobe light support 1H. The remote 11 can be held in the user's hand while needed, and placed on a surface when not in use. The remote 11 directly controls the operation of the strobe light. In the preferred embodiment, there are three music modes:

music 1: sound active mode, light off; music 2: sound active mode, dynamic; and music 3: sound active mode, strobe effects. In lieu of music, the strobe can be set to burst mode where the light will flash at a regular interval. The strobe also displays red, green, and blue light individually, or in combination, as selected by the remote. In the preferred embodiment, there are a total of seven color modes.

The user then lays his head on the pillow 5 and pillowcase 6, and, if desired, activates the vibrating element 8 by switching the control 8A to the on position, and rotating the wheel to the desired vibrational intensity. The vibrating egg 8B is disposed beneath the pillowcase 6, on top of the pillow 5, so as to be directly beneath the user's head while he is lying down, although the vibrating egg 8B can be disposed in a plurality of locations beneath the pillowcase 6 as desired. One of ordinary skill would understand that the vibrating egg 8B could be disposed outside of the pillowcase 6, if desired. The vibrating element control 8A can then be clipped to the left wall 1B or right wall 1C of the housing 1, or simply held in the user's hand during use.

After a period of time has elapsed (at least 15 minutes), the user should begin to feel more relaxed, and may fall asleep. Alternatively, if a user chooses stimulating essential oils, such as rosemary, lemon, peppermint, etc., opts for higher frequency binaural sounds, and high intensity light effects, he would eventually become more alert. The aromatherapy diffuser in this example will continue to run until the reservoir is empty. Other diffusers have built-in timers that deactivate the diffuser after a particular duration, for example, 20 minutes. One of ordinary skill would understand that a variety of different diffusers may be used with this invention, and not limited to the specific model mentioned above.

It is not necessary for the diffuser 2, the binaural sounds, meditation sounds, or music being played through the speakers 3 and 4, the vibrating element 8, and the strobe light 10 to be in use simultaneously; one of ordinary skill would assume that these features can be used independently or in any combination, depending on the therapy desired. The strobe light 10 in this example is sound-activated, so that the light patterns are complementary to the sounds output by the speakers 3 and 4, depending on the mode of operation selected with the remote. One of ordinary skill would understand that a variety of different strobe lights may be used with this invention, and not limited to the specific model mentioned above.

It is understood that the embodiment presented in this description and drawings is meant to be exemplary. Embodiments of the present invention can comprise any combination of compatible features shown in the various figures, and these embodiments should not be limited to those expressly illustrated and discussed, and without departing from the scope and spirit of the invention as set forth in the following claims.

For the purposes of the specification and claims of the present invention, the masculine grammatical gender subsumes the feminine gender.

I claim:

1. An aromatherapy apparatus comprising:
   a housing comprising a bottom wall, a left wall, a right wall, and a rear wall;
   a contoured shape-memory foam pillow located on said bottom wall, said pillow disposed within a fabric pillowcase;
   a pair of speakers including an audio input cable, each said speaker located on a respective speaker support piece attached to said housing;
   an aromatherapy diffuser located on a diffuser support piece attached to said housing;
   a vibrating element for imparting vibrations to said pillow;
   a strobe light located on a strobe light support piece attached to said housing; and
   a canopy secured to said housing.

2. The apparatus of claim 1, wherein said vibrating element comprises a vibrating egg disposed inside or outside said pillowcase.

3. The apparatus of claim 1, wherein said vibrating element includes a control configured to be handheld or secured to said housing.

4. The apparatus of claim 1, wherein said housing is fabricated from wood or plastic, or a combination thereof.

5. The apparatus of claim 1, wherein one of the said speaker support pieces is attached to said left wall, and the other of the said speaker support pieces is attached to said right wall; wherein said diffuser support piece is attached to said rear wall; and wherein said strobe light support piece is attached to said rear wall.

6. The apparatus of claim 1, wherein said canopy is secured to said rear wall.

7. The apparatus of claim 1, wherein said speakers are connected to a smartphone or portable music player via the audio input cable.

8. The apparatus of claim 1, wherein said aromatherapy diffuser contains a mixture of water and essential oils.

9. The apparatus of claim 1, wherein said strobe light outputs a visual light pattern.

10. The apparatus of claim 1, wherein the left wall and the bottom wall each have a rectangular shape having two long edges and two short edges, and wherein one of the long edges of the left wall is joined to one of the short edges of the bottom wall such that the left wall and bottom wall are perpendicular to each other.

11. The apparatus of claim 1, wherein the right wall and the bottom wall each have a rectangular shape having two long edges and two short edges, and wherein one of the long edges of the right wall is joined to one of the short edges of the bottom wall such that the right wall and bottom wall are perpendicular to each other.

12. The apparatus of claim 1, wherein the rear wall and the bottom wall each have a rectangular shape having two long edges and two short edges, and wherein one of the long edges of the rear wall is joined to one of the long edges of the bottom wall such that the rear wall and bottom wall are perpendicular to each other.

13. The apparatus of claim 1, wherein the left wall, the right wall, and the rear wall each have a rectangular shape having two long edges and two short edges, and wherein one of the short edges of the rear wall is joined to one of the short edges of the left wall at a ninety-degree angle and the other of the short edges of the rear wall is joined to one of the short edges of the right wall at a ninety-degree angle.

14. The apparatus of claim 1, wherein said fabric pillowcase is comprised of a temperature-regulating fabric.

15. A method of using an aromatherapy apparatus, the method comprising:
    a user adding water to an aromatherapy diffuser,
    said aromatherapy diffuser disposed on a support piece of a housing, said housing in the form of an open container;
    said user adding one or more essential oils to the water in said aromatherapy diffuser, and activating said aromatherapy diffuser;

said user connecting a user-supplied smartphone, mobile device, or portable music player to a pair of portable stereo speakers, each of said speakers disposed on a respective support piece of said housing, and said user activating one of a music application or binaural beats application preinstalled on said user's smartphone, mobile device, or portable music player;

said user activating a strobe light, said strobe light disposed on a strobe light support piece of said housing;

said user deploying a canopy secured to said housing;

said user laying his head down on a shape memory foam pillow, said pillow disposed within said housing, and said pillow encased within a temperature-regulating fabric pillowcase; and said user activating a vibrating element for imparting vibrations to said pillow.

\* \* \* \* \*